(12) United States Patent
Yuen

(10) Patent No.: US 8,681,006 B2
(45) Date of Patent: Mar. 25, 2014

(54) SWIM MONITOR USING A THREE-AXIS ACCELEROMETER

(75) Inventor: Paul Anthony Yuen, New Territories (CN)

(73) Assignee: Dayton Technologies Limited, New Territories, Hong Kong (CN)

( * ) Notice: Subject to any disclaimer, the term of this patent is extended or adjusted under 35 U.S.C. 154(b) by 206 days.

(21) Appl. No.: 13/262,073

(22) PCT Filed: Apr. 1, 2010

(86) PCT No.: PCT/IB2010/051432
§ 371 (c)(1),
(2), (4) Date: Sep. 29, 2011

(87) PCT Pub. No.: WO2010/113135
PCT Pub. Date: Oct. 7, 2010

(65) Prior Publication Data
US 2012/0019381 A1    Jan. 26, 2012

(30) Foreign Application Priority Data
Apr. 1, 2009 (HK) .................................. 09103086.0

(51) Int. Cl.
*G08B 21/00* (2006.01)
(52) U.S. Cl.
USPC ........................................ 340/573.1; 434/254
(58) Field of Classification Search
USPC ................ 340/540, 573.1; 454/247, 254, 258
See application file for complete search history.

(56) References Cited

U.S. PATENT DOCUMENTS 5,685,722 A * 11/1997 Taba .............................. 434/254
5,685,723 A    11/1997 Ladin et al.
6,305,221 B1   10/2001 Hutchings
2003/0138763 A1  7/2003 Roncalez et al.

FOREIGN PATENT DOCUMENTS

CN    2380267 Y    5/2000
EP    1 623 743 A1  2/2006

OTHER PUBLICATIONS

International Search Report (PCT/ISA/210) issued on Aug. 26, 2010, by Chinese Patent Office as the International Searching Authority for International Application No. PCT/IB2010/051432.

* cited by examiner

*Primary Examiner* — Jeffery Hofsass
(74) *Attorney, Agent, or Firm* — Buchanan Ingersoll & Rooney PC

(57) ABSTRACT

A swim monitor comprising a motion sensing device and a controller is provided. The motion sensing device is capable of detecting motion in a plurality of mutually orthogonal axes and the controller is arranged to capture motion data generated by the motion sensing device and to generate swim motion information with reference to the motion data collected. The controller is arranged to generate swim style information with reference to a rhythmic motion pattern detected in at least one selected motion direction. Such a swim monitor provides a compact device for swim monitoring and a simple solution to proved swim style information.

20 Claims, 9 Drawing Sheets

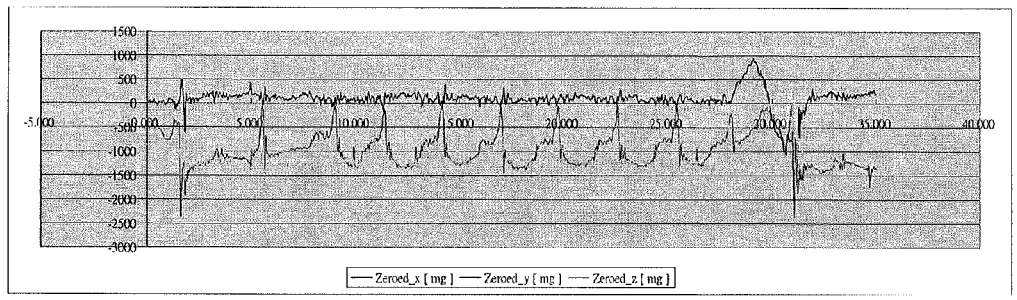
FIGURE 2 – TYPICAL BREAST STROKE PATTERN
Breast Stroke Simplified Pattern
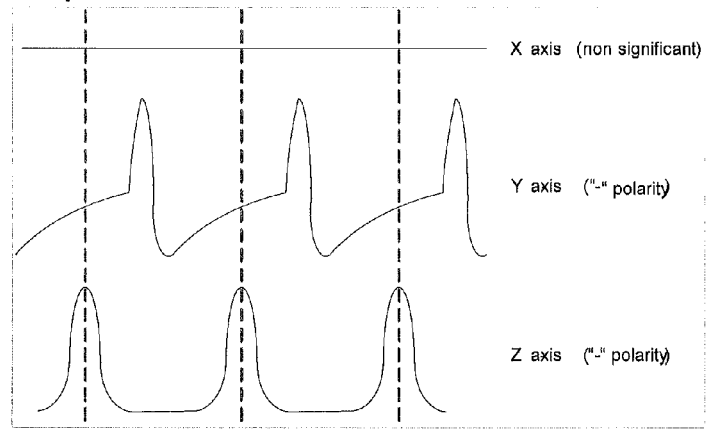
FIGURE 2A
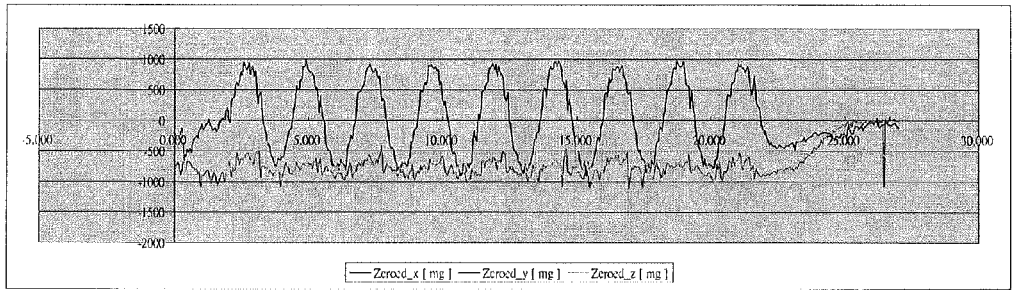
FIGURE 3 – TYPICAL FREESTYLE STROKE PATTERN

Freestyle Stroke Simplified Pattern
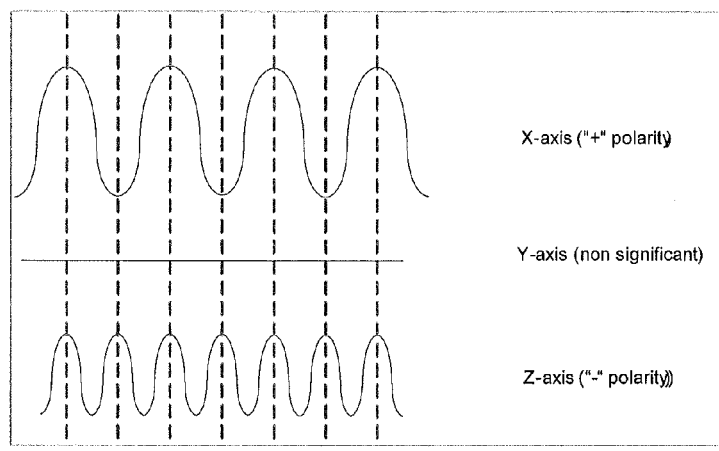
FIGURE 3A
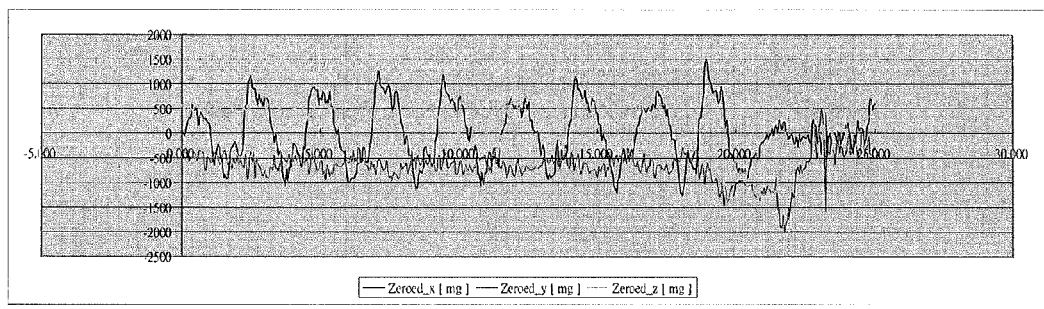
FIGURE 4 – TYPICAL BACK STROKE PATTERN

Back Stroke Simplified Pattern
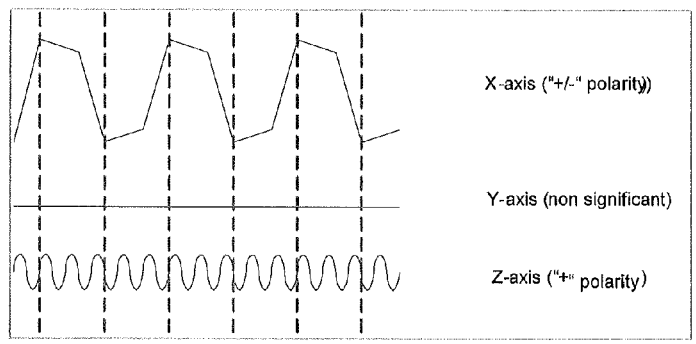
FIGURE 4A
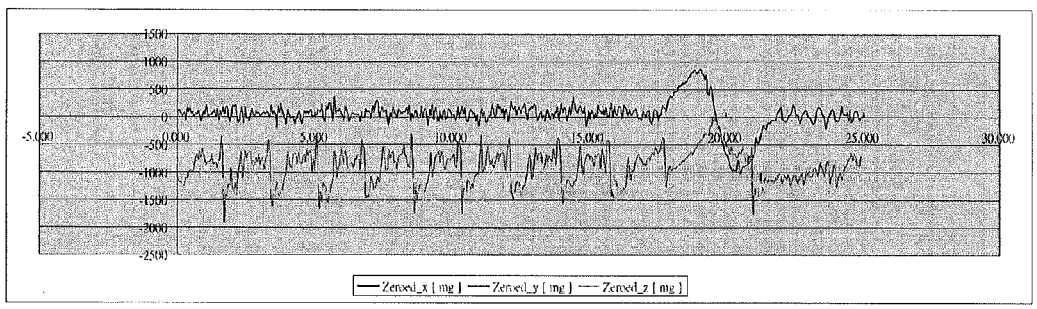
FIGURE 5 – TYPICAL BUTTERFLY STROKE PATTERN
Butterfly Stroke Simplified Pattern
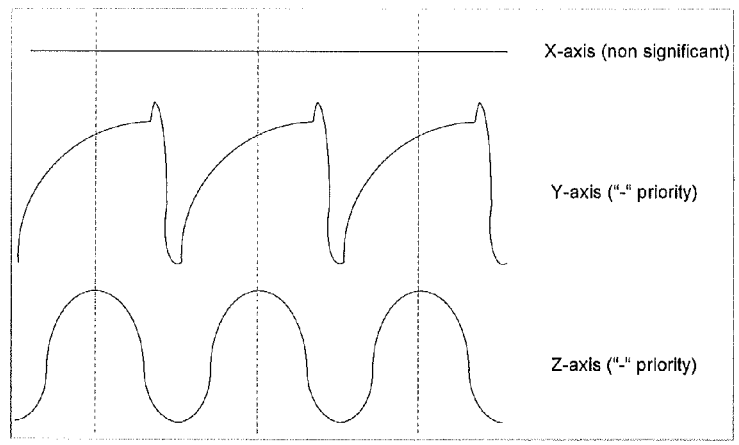
FIGURE 5A

FIGURE 7 – TYPICAL STROKE PULSE

SWIM MONITOR USING A THREE-AXIS ACCELEROMETER

FIELD OF THE INVENTION

The present invention relates to sports monitors and more particularly to swim monitors. More specifically, although not solely limited thereto, this invention relates to swim monitors arranged to detect swim styles, and to swim monitors with wireless data transmission capability.

BACKGROUND OF THE INVENTION

Sports monitors for capturing and analyzing relevant sporting data and information for display are becoming increasingly popular. Sports monitors are typically worn by persons doing a physical sport and are usually configured to capture both physiological data relating to the physiological state of the person wearing the monitor and performance data relating to the exercise. The captured physiological data can be used to provide instantaneous feedback on the physical state of the exerciser as well as for subsequent fitness analysis. On the other hand, the captured performance data can provide useful data and information for analyzing the performance or physical fitness of the person performing the sport, and could be used for customizing programs to improve performance of the person doing the exercise.

Among the various physical sports, swimming is well recognized as very beneficial because of its balanced and low impact characteristics. Although swim monitors are available, the performance and functionalities of conventional swim monitors is somewhat limited. For example, conventional swim monitors require activation by a swimmer in order to trigger data capture. Also, conventional monitors do not provide information on swim styles nor performance parameters relating to swim styles. Furthermore, conventional swim monitors are usually arranged for transient display of swim parameters and are not adapted for transferring captured data or parameter to an external device for storage or further processing due to water leakage concerns. Although wireless data transmission arrangement appears to be a possible alternative to overcome water leakage problems, the heavy attenuation of radio signals under water is an apparent obstacle to using wireless solution for a swim monitor.

Therefore, it will be highly desirable if swim monitors having at least some of the shortcomings of conventional swim monitor mitigated can be provided.

SUMMARY OF THE INVENTION

According to the present invention, there is provided a swim monitor comprising a motion sensing device and a controller, the motion sensing device being capable of detecting motion in a plurality of mutually orthogonal axes and the controller being arranged to collect motion data generated by the motion sensing device and to generate swim motion information with reference to the motion data collected, wherein the controller is arranged to generate swim style information with reference to a rhythmic motion pattern detected in at least one selected motion direction.

A swim monitor arranged to detect rhythmic motion pattern in at least one selected motion direction among a plurality of orthogonal motion axes facilitate quick determination of swim style using a simple algorithm.

The motion sensing device may comprise a 3-axis accelerometer which provides a simple and compact hardware solution to the making of a swim monitor.

The at least one selected motion direction may be one of the plurality of mutually orthogonal axes. Selecting a motion direction which is one of the mutually orthogonal axes means more efficient processing by the controller.

The swim monitor may be adapted to be worn on a swimmer such that the mutually orthogonal axes correspond to vertical, forward and lateral directions during swimming. Such an adaptation means the orthogonal axes of the motion sensing device and the motion axes are readily aligned when the swim monitor is duly worn.

The controller may be arranged to categorize motion data collected by the motion device as swim motion data, or motion characteristic of swimming, if the motion data collected exhibit a rhythmic pattern in at least two orthogonal motion directions.

These and other features and advantages of the invention will be apparent from the description below.

BRIEF DESCRIPTION OF THE DRAWINGS

An exemplary embodiment of the present invention is described by way of example below and with reference to the accompanying figures, in which:—

FIG. 2 is an exemplary motion amplitude chart showing the relative motion amplitudes in three orthogonal axes (X, Y, Z) typical of a sequence of breast strokes, FIG. 3 is an exemplary motion amplitude chart typical of a sequence of freestyle strokes, FIG. 4 is an exemplary motion amplitude chart typical of a sequence of back strokes, FIG. 5 is an exemplary motion amplitude chart typical of a sequence of butterfly strokes, FIGS. 2A to 5A are respectively simplified schematic signal diagrams of FIGS. 2 to 5 for easier reference.

DETAILED DESCRIPTION OF EXEMPLARY EMBODIMENTS

Swimming requires timely coordination of various body parts in order to perform effectively. Because of its low-impact nature and extensive requirements of body coordination, it is generally recognized as one of the most beneficial type of physical or cardiovascular sports. Among the various swim styles known, free-style, butterfly, breast stroke and back stroke are generally considered as the most popular swim styles which are frequently performed by the public, although there are of course other swim styles which are practiced.

Each of the most popular swim styles is characterized by its specific movement patterns. For example, free-style is characterized by timely and synchronized side paddling of arms and legs on opposite sides of the body trunk of a swimmer to do front crawls. At the same time, the freestyle swimmer needs to turn the head periodically to breathe while the body is moving forward. A butterfly swimmer needs to perform synchronized striking on water to lift the body trunk out of water, to dive in and then to do a dolphin-like tail kick to prepare for the next arm striking. When doing breast strokes, a swimmer needs to do frog-like crawls with the chest facing the bottom of a swimming pool and the torso not rotating. Back-stroke is similar to freestyle except that the chest of a swimming is upwards.

Figure 1:
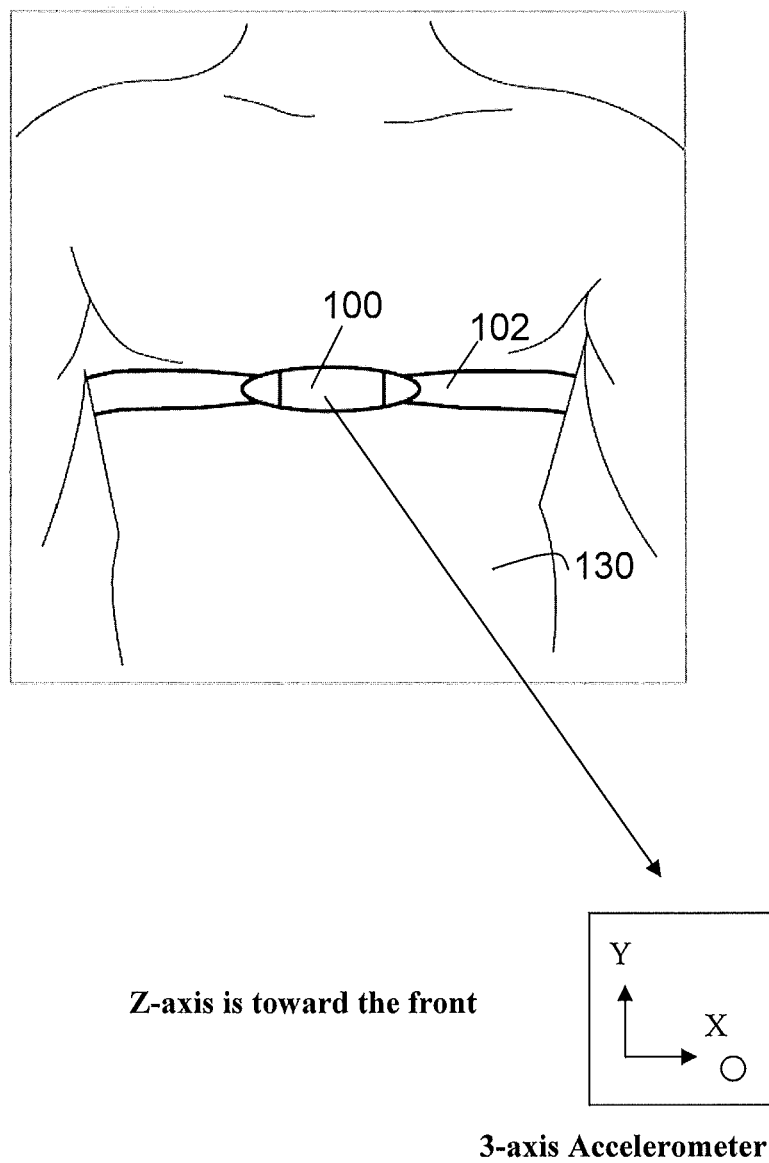
FIG. 1 depicts a swimmer wearing an embodiment of the swim monitor of the present invention.

Referring to FIG. 1, a swim monitor 100 comprising a 3-axis accelerometer 110 as an example of a motion sensing device is shown. The swim monitor is mounted on a chest strap 102 and is adapted to be worn on the body trunk of a swimmer 130 by means of the chest strap, similar to the wearing of a heart rate monitor commonly seen in fitness centers. The swim monitor is arranged so that, when the swim monitor is worn, the 3-axis accelerometer is aligned with one of the orthogonal axes (say Y-axis) parallel to the body axis and positive towards the head portion, another axis (say X-axis) is orthogonal to the Y-axis and extends sideways of the body trunk, and the third axis (say Z-axis) is orthogonal to both the X- and Y-axes. In general, the orthogonal axes correspond to forward, vertical and side directions in swimming.

In use, the Y-axis is aligned with the direction of forward body movement, which is usually the direction towards pool end, the X-axis is in the lateral direction which is usually towards the pool sides, and the Z-axis is either towards the pool bottom or sky. Of course, the designation of X-, Y- and Z-axes herein is purely arbitrary for convenience only and could be re-labeled using other names, symbol or designation without loss of generality.

Swim Style Detection

FIGS. 2-5 are amplitudes in the X-, Y- and Z-axes recorded by the swim monitor for sequences of breast stroke, freestyle, back stroke and butterfly movements respectively. Upon a systematic study of the movement patterns of the various swimming styles, it is noted that the movements of the four most commonly practiced swim styles can be decomposed into components in the 3-othorgonal axes more particularly set out in summary in table 1 below.

TABLE 1

| Swim Style | Significant Group | | | | Non-significant Group |
|---|---|---|---|---|---|
| | Dominant Pattern | | Supplementary Pattern | | |
| | Axis | Polarity | Axis | Polarity | Axis |
| Breast | Y | − | Z | − | X |
| Freestyle | X | + | Z | − | Y |
| Back | X | +/− | Z | + | Y |
| Butterfly | Y | − | Z | − | X |

Upon a review of the movement characteristics of the various swimming styles as set out in Table 1, it is noted that each of commonly practiced swim styles, for example, free-style, breast stroke, butterfly, and back stroke, can be characterized by their respective characteristic rhythmic movement patterns along two orthogonal axes. For example, it is observed that breast stroke and butterfly styles are characterized by rhythmic movements of the body trunk in the Y and Z directions, with the Y-axis motion being more dominant than the Z-direction. For both breast stroke and butterfly, the Z-axis motion is supplementary, and the X-axis motion is practically non-significant.

On the other hand, freestyle and back stroke are characterized by rhythmic movement patterns of the body trunk in the X and Z directions, with movement in the X-axis being more dominant than motion in the Z-direction. For both free-style and backstroke, the Z-axis motion is supplementary and the Y-axis motion is practically non-significant. As the filed data were captures during actual swimming, the X, Y and Z directions are respectively the forward (pool end), sideward (pool side), and upward (orthogonal to water surface) directions.

In this description and other parts of this document, a direction is dominant if the motion in that direction is rhythmic and the amplitudes of its motion peaks are the highest compared to other rhythmic motions. A direction is non-significant if it demonstrates no or minimal periodic character. A direction is supplementary if the motion is rhythmic while the amplitudes of its peak motion are less than that of the dominant direction.

Swim Monitor

Figure 6:
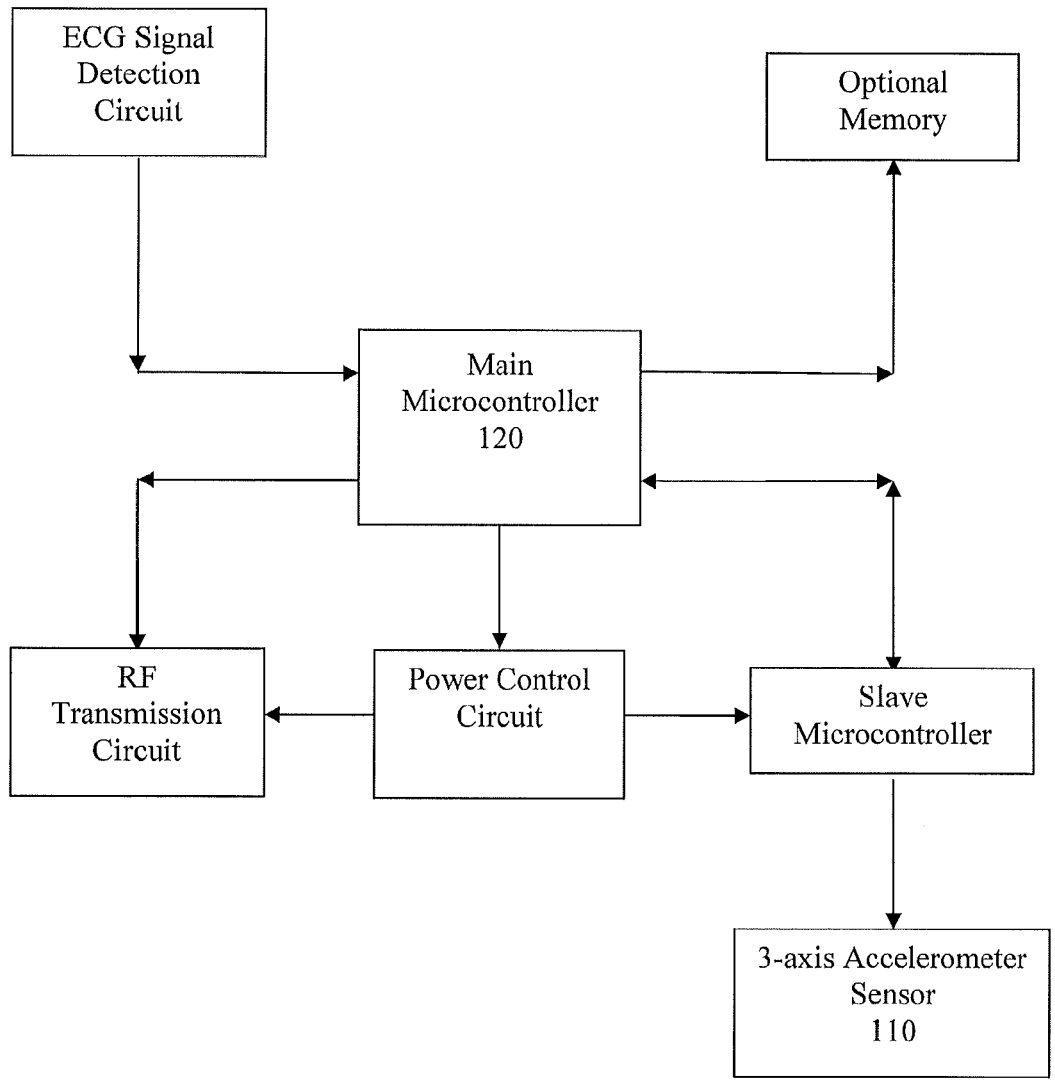
FIG. 6 is a functional block diagram of an exemplary swim monitor comprising a 3-axis accelerometer connected to a main micro-controller.

To determine swim styles and other related performance parameters, an exemplary swim monitor comprising a 3-axis accelerometer connected with reference to the functional block diagram of FIG. 6 is provided as an embodiment of the invention. Referring to FIG. 6, the swim monitor comprises a 3-axis accelerometer which is connected to a main microprocessor via a slave microprocessor. A memory device for storing captured data is connected to the main microprocessor, an optional heart rate monitor or detection circuit is also connected to the main microprocessor for detecting heart rate signals during exercise. To facilitate wireless data transfer between the swim monitor and an external swim data processing station, a radio-frequency (RF) circuit is connected. The swim monitor is configured to obtain swim motion data in 3 orthogonal axes and the data thus obtained are stored in the memory device for processing.

To determine the individual swim style being performed, the main microcontroller is configured to examine the swim motion data stored in the memory device to identify the dominant direction with reference to swim data collected in the mutually orthogonal axes.

If the dominant motion direction is the X-axis, the style will be determined as either freestyle or back stroke. If the dominant motion direction is the Y-axis, the style will be determined as either breast stroke or butterfly.

To distinguish between freestyle and back stroke in the case of a dominant X-axis swimming motion, the microcontroller will look at the polarity of X-axis motion, if the motion polarity is negative, the style is back stroke. Alternatively, the micro-controller can look at the polarity of the supplementary Z-direction signal—a negative polarity means freestyle while a positive polarity means back stroke. In arriving at the above, it is noted that the Z direction motion for freestyle is primarily negative while the Z direction motion for back stroke is primarily positive.

Although it is noted that the rhythmic motion patterns of butterfly and breast stroke are similar in both the Y- and Z-axes, it is noted, for example, from FIGS. 2 and 5, that there is a higher concentration (or longer duration) of high amplitude motion in the Y axis, especially in the vicinity of the amplitude peaks for butterfly. Such a concentration reflects the extended period that the body trunk of a swimmer is out of water within a stroke cycle fact, compared to the minimal out-of-water duration incase of breast stroke.

To distinguish between breast stroke and butterfly in the case of a dominant Y-axis swimming motion, the microcontroller will look for a population or concentration of high amplitude motion components in the vicinity of motion peaks in the dominant direction. If the concentration fulfills a predetermined criterion, for example, a predetermined threshold criterion, the microcontroller will determine that the style is butterfly. For example, a threshold could be set that the percentage of motion amplitude having amplitude of at least A % of the peak amplitude exceeds B % for a butterfly determination. For example, A could be 60 and B could be 50, or other appropriate parametric values to be determined. Naturally, the parameters could be empirically set or adjusted.

Stroke Detection and Count

Figure 7:
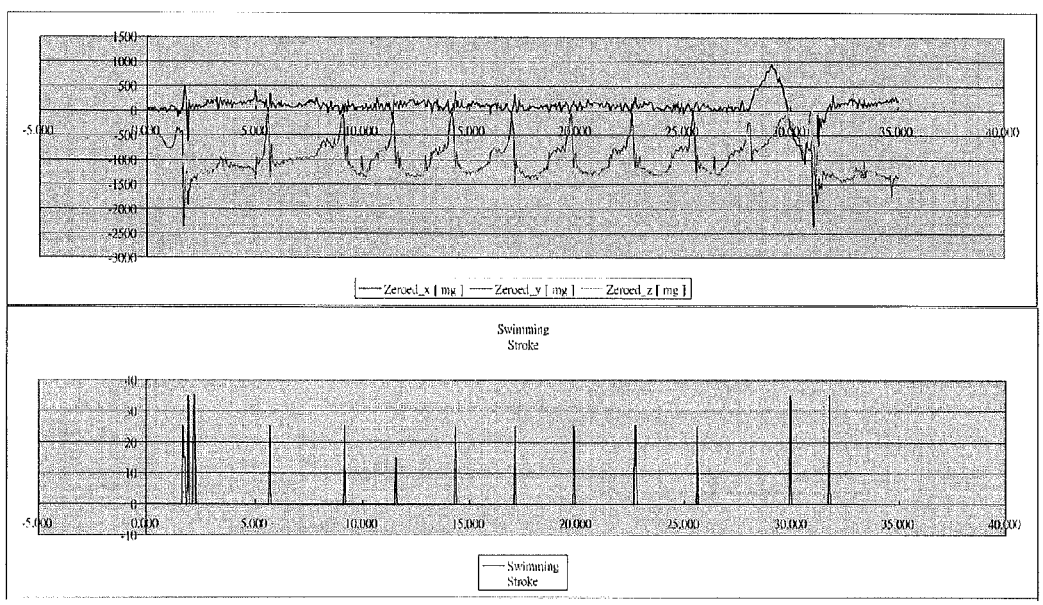
FIG. 7 is a chart showing pulse counts.

Stroke counts provide useful information on the performance of a swimmer. As an optional feature, the swim monitor is provided with means to determine stroke counts, for example, stroke-per-lap. To determine stroke counts, the micro-controller is configured to detect signals which signify start and end of a lap, for example, turns or jump, and then to measure the number of strokes between turns or between a turn and a jump. Specifically, the main micro-controller is configured to look for number of stroke cycles between turns or between a turn and a jump. For example, a stroke will be counted on occurrence of an amplitude peak in a dominant direction. The number of strokes could be obtained by calculating the number of stroke pulses occurred, as shown for example in FIG. 7. The pulse information could be obtained, for example, by looking for signal spikes exceeding a threshold amplitude value from the captured swim data.

Turn Detection

Turns provide useful information, such as statistical information, on swimming for reference by a swimmer or for coaching. For example, the number of laps undertaken could be determined with respect to turn counts and the time per lap could be determined by taking time between consecutive laps.

To identify turns, or to distinguish a turn from a normal swim stroke, the microcontroller ("MCU") would look for a motion signifying a turn. Referring to the algorithm of FIG. 8, a turn is determined by detection of a change of the Z-axis from vertical to horizontal and then from horizontal back to vertical, or the Y-axis is changed from horizontal to vertical and then from vertical back to horizontal.

In the above regard, it should be appreciated that when reference is made herein to a change from horizontal to vertical or vice versa, the change means an intuitive change of body inclination and does not require a full 90 degree change in geometric orientation. For example, a change of 45-60 degrees in body inclination could be accepted as a sufficient threshold to report a detection of such a change.

Jump Detection

To identify a jump, the microcontroller will look for a sudden change or an abrupt change of motion corresponding to a jump motion. Referring to the algorithm of FIG. 8, the slave MCU is configured to detect a jump signal by looking for a sudden motion change signal which could be signified by, for example, i) a sudden change of the Z-axis from horizontal to vertical, and/or ii) a sudden change of Y-axis from vertical to horizontal, while the X-axis remains horizontal.

Auto Start/Stop

The swim monitor is also provided with an optional feature of automatic timing, so that a swimmer does not have to start and stop a timer manually. To facilitate automatic timer start, the MCU is configured to detect a jump, and to start timing upon detection of a jump.

To stop timing, the MCU is configured to stop the time when no swimming is detected. No swimming is detected, for example, when there is no stroke count and/or when no swim style is detected, and/or when X- and Z-axes are both horizontal, and/or when Y-axis is changed to vertical and kept vertical.

1$^{st}$ Exemplary Embodiment

Figure 8:
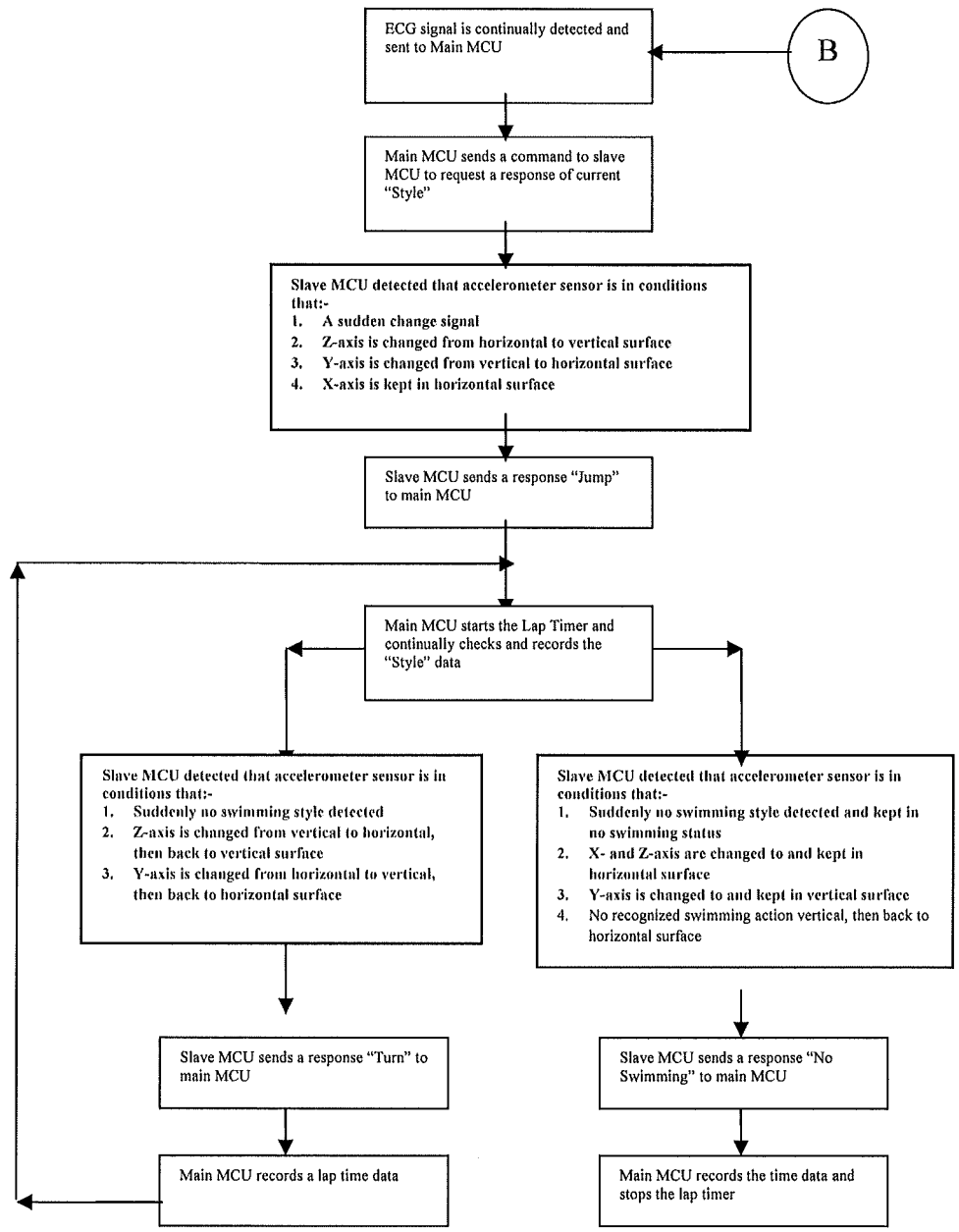
FIG. 8 is a flow chart showing an exemplary algorithm for lap timing with automatic start stop.

An exemplary embodiment of a swim monitor comprising the features mentioned above will now be depicted with reference to the block diagram of FIG. 6 and the flowchart of FIG. 8. In this embodiment, a heart rate monitor is included as an optional feature to monitor the instantaneous physiological state of a swimmer.

Referring to FIGS. 6 and 8, the main MCU is configured to detect heart rate signals in the form of ECG signals. Upon detection of ECG signals, the main MCU will request the slave MCU to standby and to provide swimming related information once swimming is detected. Upon receipt of the request from the main MCU, the slave MCU will monitor the accelerometer to detect a jump, which signifies the beginning of a new swim session. Upon successful detection of a jump, the slave MCU will inform the main MCU of such detection, and the main MCU will start the lap timer and cause the slave MCU to capture motion data in the orthogonal axes and to determine swim style.

After the collection of swim data has been actuated by the main MCU, the MCU will begin the process of collecting motion data from the accelerometer. At the same time, the slave MCU will look for turns and inform the main MCU of the detection of a turn. The main MCU will then process the turn data information into lap counts and lap timing. This process will repeat until a swim stop is detected. When swim stop is detected, the slave MCU will inform the main MCU of such detection and the main MCU will stop the timer.

Data Transfer

Due to its very own nature, a swim monitor is immersed in water during most of the time of its normal use. Good water tightness is therefore essential for the protection of the electronic components inside the swim monitor to ensure durability and reliability. The water tightness requirements would mean that data transfer to and from the swim monitor, for example, transfer of data from the swim monitor to an external device for further data processing or storage, or transfer of data to the MCUs for updates on algorithms or customized profiles would preferably be wireless. However, it is noted that wireless data transfer from an immersed device is highly unstable due to the high signal attenuation by water.

2$^{nd}$ Exemplary Embodiment

The swim monitor of the present invention is configured with an optional data transfer arrangement to mitigate difficulty of wireless data transmission or reception. To equip with wireless data transmission capability, the swim monitor of FIG. 6 is provided with an RF transmission circuit which is connected to the main MCU and is controlled by the MCU through a power control circuit.

Figure 9:
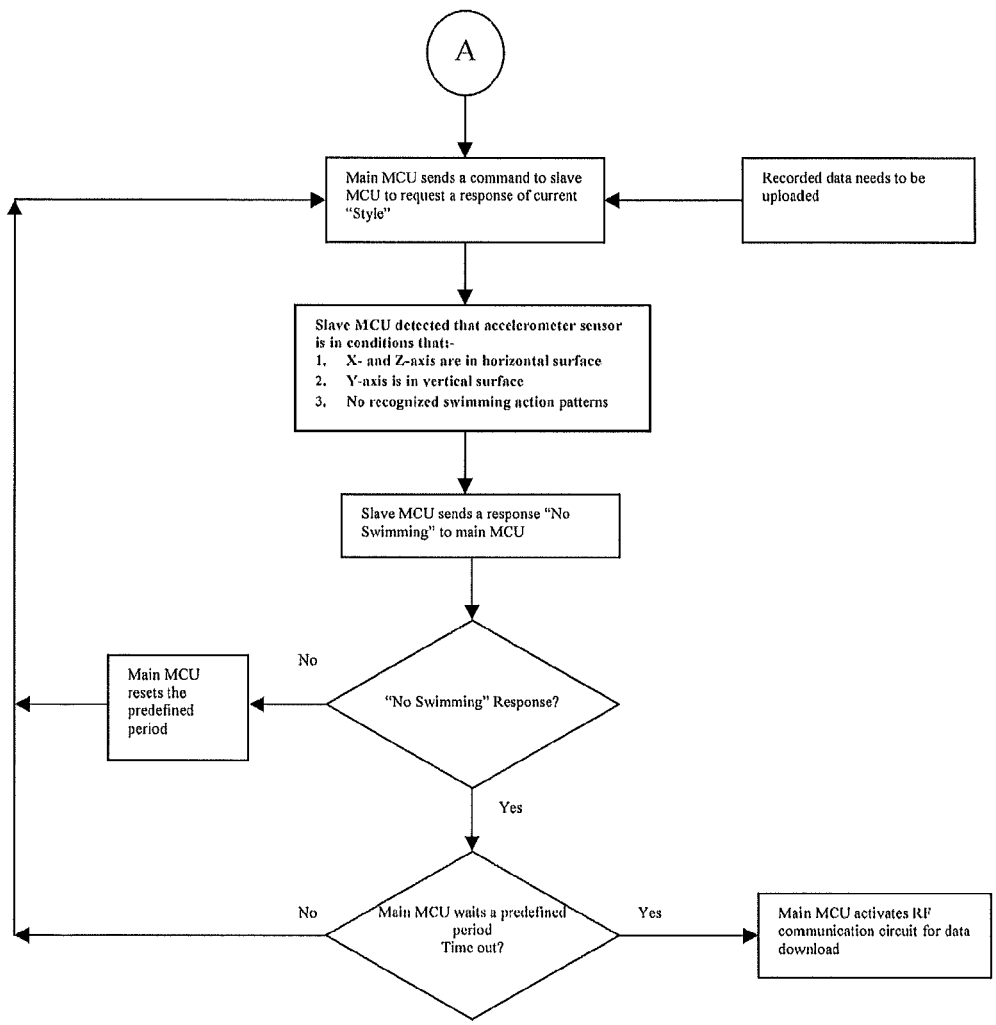
FIG. 9 is a flow chart showing an exemplary algorithm to facilitate data transmission when swimming has stopped and when the device is out of water.

Referring FIG. 9 which shows a portion of the operating algorithm after swim data have been captured and a termination of swimming is detected (in other words a "no swimming" signal is detected), the slave MCU will send the no swimming signal to the main MCU. The main MCU will wait for a predefined period and then activate the RF communication circuit to download data to an external controller or station. If swimming is detected before the expiry of the predefined period, the main MCU will operate again to capture swimming data again.

The use of a main micro-controller and a slave controller in this embodiment is for division of labour between the two controllers and is especially for optimized power saving. In an alternative embodiment, a single micro-controller is used for control of the accelerometer and other components.

Auto Power Saving

Like many portable electronic products, power saving is essential for extending the operating life of a swim monitor, especially if a swim monitor is sealed for water tightness.

Therefore, it is beneficial is power utilization can be kept at a minimum when there the swim monitor is not in use or when there is no swimming for an extended period of time.

3rd Exemplary Embodiment

Figure 10:
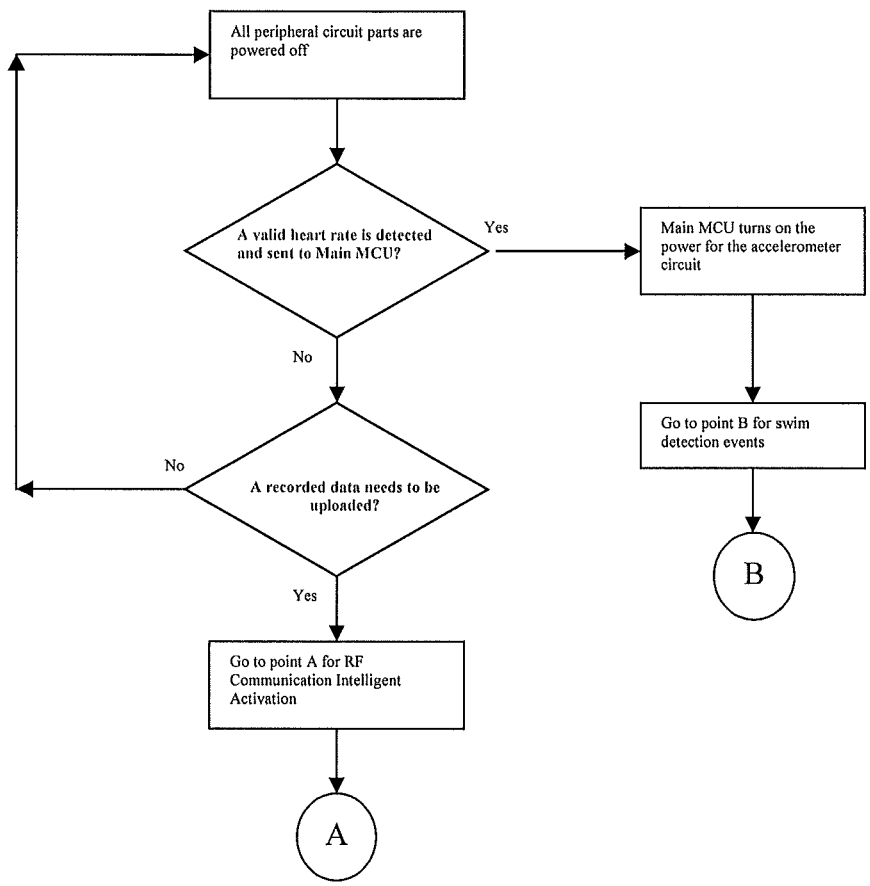
FIG. 10 is a flow chart showing an exemplary algorithm to facilitate power saving.

To minimize power utilization, the algorithm of FIG. 10 is arranged such that the swim monitor is kept at a power off or dormant state with no or minimum power supply to non-essential peripheral circuit parts. Among the various peripheral components, the accelerometer is probably the most power hungry component and is therefore powered off unless and until it is required to function.

Referring to FIG. 10, the main MCU will turn on power supply to the accelerometer upon detection of ECG signals. If no ECG signal is detected, it is likely that the swim monitor is not in use, for example, it is not being chest worn. After power supply to the accelerometer ahs been turned on, the main MCU will proceed with the algorithm of FIG. 8 to look for swim related data and process accordingly. If no ECG is detected, the main MCU will also check internally whether there are data awaiting disposal, for example, up-loading to an external device. If positive, the main MCU will proceed with data transfer, for example, following the algorithm of FIG. 9.

Although embodiments of the swim monitor have been described with reference to a chest worn device, it will be appreciated that the swim monitor can be implemented with other attachment means, for example, by wrist-worn attachment means.

The invention claimed is:

1. A swim monitor, comprising:
a motion sensing device and a controller, the motion sensing device including a 3-axis accelerometer to detect motion in a plurality of mutually orthogonal axes and the controller being arranged to capture motion data generated by the motion sensing device and to generate swim motion information with reference to the motion data collected, wherein the controller is arranged to generate swim style information with reference to a rhythmic motion pattern detected in or parallel to at least one selected motion direction, the at least one selected motion direction being one of the plurality of mutually orthogonal axes.

2. A swim monitor according to claim 1, wherein the swim monitor is adapted to be worn on a swimmer such that the mutually orthogonal axes correspond to vertical, forward and lateral directions during swimming.

3. A swim monitor according to claim 1, wherein the controller is arranged to categorize motion data collected by the motion device as swim motion data, or motion characteristic of swimming, if the motion data collected exhibit a rhythmic pattern in at least two orthogonal motion directions.

4. A swim monitor according to claim 1, wherein the controller is arranged to detect a dominant motion direction between the two orthogonal motion directions each exhibiting a rhythmic pattern and to provide swim style information with reference to the dominant motion direction.

5. A swim monitor according to claim 4, wherein the controller is arranged to provide information on swim style with reference to concentration of motion exceeding a threshold value in the dominant motion direction.

6. A swim monitor according to claim 1, wherein the controller is arranged to determine swimming style with reference to motion data collected in a plurality or mutually orthogonal axis.

7. A swim monitor according to claim 1, wherein the controller is arranged to process the motion data collected by the motion sensing device to determine whether there is periodic or rhythmic motion characteristic of a known swimming style, and to determine whether there is swimming according to outcome of determination.

8. A swim monitor according to claim 1, wherein the motion data collected comprises motion direction which is represented by signal polarity.

9. A swim monitor according to claim 8, wherein the motion sensing device and the controller are arranged to distinguish between free style and back style with reference to motion polarity in a predetermined axis, the predetermined axis being orthogonal to water surface.

10. A swim monitor according to claim 8, wherein the motion sensing device and the controller are arranged to distinguish between breast style and free style with reference to motion in one of three predetermined orthogonal axes, the one axis being parallel to water surface and orthogonal to swimming direction.

11. A swim monitor according to claim 1, wherein the motion sensing device and the controller are arranged to detect a jump with reference to a sudden change of one motion axis from horizontal to vertical and another motion axis from vertical to horizontal.

12. A swim monitor according to claim 1, wherein the controller is arranged to detect start and stop of swim, and to activate transmission of swim data to an external data collector within a predetermined delay period after swimming has stopped.

13. A swim monitor according to claim 12, further comprising a wireless transmitter for transmitting swim data to the external data collector, the wireless transmitter being activated within a prescribed delay time after detection of a swim stop.

14. A swim monitor according to claim 13, wherein the swim monitor is mounted on a chest strap, and the motion sensing device is adapted to detect swimming motion when the swim monitor is chest worn.

15. A swim monitor according to claim 1, wherein the swim monitor further includes a heart rate monitor.

16. A swim monitor according to claim 15, wherein the controller is arranged to turn on power supply to the motion sensing device upon detection of heart rate signals.

17. A swim monitor according to claim 1, wherein the controller is arranged to perform lap counts with reference to number of turns detected during swimming.

18. A swim monitor according to claim 17, wherein the controller is arranged to perform lap speed calculation by measuring time between turns.

19. A swim monitor according to claim 1, wherein the swim monitor further includes activation means to activate operation of the motion sensing device upon detection of a sequence of movements which are characteristic of jumping.

20. A swim monitor according to claim 1, further comprising:
a wireless transmitter, the wireless transmitter being connected to the controller for data transmission from the swim monitor, wherein the controller is arranged to cause transmission of data from the swim monitor after the controller has detected a swim stop and after expiry of a predetermined interval.

* * * * *